(12) United States Patent
Sugimoto et al.

(10) Patent No.: US 7,749,538 B2
(45) Date of Patent: Jul. 6, 2010

(54) MOLDED OBJECT HAVING HIGH PULLULAN CONTENT, PROCESS FOR THE PRODUCING THE SAME, AND USE THEREOF

(75) Inventors: Toshiyuki Sugimoto, Okayama (JP); Toshio Miyake, Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 641 days.

(21) Appl. No.: 10/475,993

(22) PCT Filed: Apr. 25, 2002

(86) PCT No.: PCT/JP02/04165

§ 371 (c)(1),
(2), (4) Date: Oct. 27, 2003

(87) PCT Pub. No.: WO02/088246

PCT Pub. Date: Nov. 7, 2002

(65) Prior Publication Data

US 2004/0158038 A1 Aug. 12, 2004

(30) Foreign Application Priority Data

Apr. 26, 2001 (JP) ............... 2001-129118
Oct. 5, 2001 (JP) ............... 2001-309758

(51) Int. Cl.
*A61K 9/14* (2006.01)
(52) U.S. Cl. .............. 424/484; 424/488; 424/439; 424/401; 424/413
(58) Field of Classification Search .............. None
See application file for complete search history.

(56) References Cited

U.S. PATENT DOCUMENTS

| | | | |
|---|---|---|---|
| 4,186,024 A * | 1/1980 | Fujimoto et al. | 106/162.9 |
| 4,562,020 A | 12/1985 | Hijiya et al. | |
| 4,623,394 A * | 11/1986 | Nakamura et al. | 106/122 |
| 5,411,945 A * | 5/1995 | Ozaki et al. | 514/23 |
| 5,518,902 A * | 5/1996 | Ozaki et al. | 435/102 |
| 5,935,636 A | 8/1999 | Nishimoto et al. | |
| 6,005,100 A * | 12/1999 | Mandai et al. | 536/123.13 |

FOREIGN PATENT DOCUMENTS

| | | |
|---|---|---|
| EP | 0 600 730 A1 | 12/1993 |
| EP | 0 628 630 A2 | 6/1994 |
| EP | 0 636 693 A2 | 7/1994 |
| EP | 0 983 727 | 3/2000 |
| EP | 1 094 092 A2 | 10/2000 |
| EP | 1 094 092 | 4/2001 |
| JP | 54-013565 | 2/1979 |
| JP | 58-216695 A | 12/1983 |
| JP | 59-111817 A | 6/1984 |
| JP | 7-170977 A | 7/1995 |
| JP | 7-213283 A | 8/1995 |
| JP | 07-246097 A | 9/1995 |
| JP | 08-041218 A | 2/1996 |
| JP | 10-179045 * | 7/1998 |
| JP | 10-179045 A | 7/1998 |
| JP | 11-302448 * | 11/1999 |
| JP | 11-302448 A | 11/1999 |
| JP | 2000-159788 A | 6/2000 |
| JP | 2000-342193 * | 12/2000 |
| JP | 2000-342193 A | 12/2000 |
| JP | 2001-048765 A | 2/2001 |
| JP | 2001-316237 A | 11/2001 |
| JP | 2002-028473 A | 1/2002 |
| JP | 2002-053674 A | 2/2002 |
| JP | 2002-053727 A | 2/2002 |
| JP | 2002-69089 A | 3/2002 |
| JP | 2002-176933 A | 6/2002 |
| WO | WO 00/50013 | 8/2000 |

OTHER PUBLICATIONS

English Translation of JP 11-302448.*
English Translation of JP 10-179045.*
English Translation of JP 2000-342193.*
Tennen-Kobunshi-no-Saishin-Riyoh-Gijutsu, R&D repoto, vol. 30, 1982, pp. 145-155.

* cited by examiner

*Primary Examiner*—Robert A Wax
*Assistant Examiner*—Hasan S Ahmed
(74) *Attorney, Agent, or Firm*—Browdy and Neimark PLLC

(57) ABSTRACT

Since conventional high pullulan content shaped products have a low stability to the change of humidity, the object of the present invention is to provide a high pullulan content shaped product having a satisfactory stability to the change of humidity, a process for producing the same, and uses. The present invention solves the above object by establishing high pullulan content shaped product with an improved stability to the change of humidity by incorporating a prescribed amount of α,α-trehalose into pullulan in preparing the high pullulan content shaped product, and a process for producing the same, and by providing uses of the high pullulan content shaped product obtainable by the process.

5 Claims, No Drawings

MOLDED OBJECT HAVING HIGH PULLULAN CONTENT, PROCESS FOR THE PRODUCING THE SAME, AND USE THEREOF

TECHNICAL FIELD

The present invention relates to a high pullulan content shaped product (hereinafter, simply abbreviated as "HPCS") having a satisfactory stability to the change of humidity, its preparation, and uses, particularly, HPCS containing at least α,α-trehalose in a prescribed amount and having a satisfactory stability to the change of humidity, its preparation, and uses.

BACKGROUND ART

There have been investigated many high molecular substances, for example, natural polysaccharides such as cellulose, starch, amylose, dextran, pullulan, carrageenan, alginic acid, mannnan, agarose, locust bean gum, xanthan gum, chitin, chitosan, etc.; and proteins such as collagen, gelatin, casein, peptide, etc., and their chemically modified products as materials of shaped products such as edible films, sheets, capsules, etc.

Particularly, water-soluble edible films have been produced from starches and polysaccharides derived from starch as materials. The typical example is a cachet. However, since such a cachet has a relatively low moisture-retaining property and resistance to humidity, and has a fragility and low transparency, the applicability of cachet have been restricted. To improve these disadvantages, the use of amylose films, which are produced by using natural amylose separated from starch, amylose obtained by hydrolyzing starch with starch-debranching enzymes, or high-amylose-starch with a high amylose content, was proposed. The films have a relatively high strength, plasticity, no oxygen-permeability, and resistance to oil. However, the amylose films are unsatisfactory in transparency and not dissolved completely even in hot water because of their low solubility. Further, the amylose films have a relatively low moisture-retaining property and resistance to humidity, and have the disadvantages of causing adhesion by absorbing moisture, causing a retrogradation of amylose during the preservation, and being fragile by drying because the films are susceptible to atmospheric humidity. Therefore, the amylose films have not been practically used.

Recently, to improve the disadvantages of starch films and amylose films, pullulan films, one of HPCS, are produced from a water-soluble natural polysaccharide, pullulan produced by *Aureobasidium pullulans*. As disclosed in "*Tennen-Kobunshi-no-Saishin-Riyoh-Gijutsu* (The latest technique using natural macromolecules)", pp. 145-155, edited by CMC publisher, Tokyo, Japan, 1982, pullulan films are colorless, transparent, tasteless, and odorless, and have a relatively high solubility in water as compared with starch films or amylose films, and a satisfactory gloss and transparency. Also, pullulan films have a satisfactory printing property and an aspect as a low-caloric food because pullulan is hardly digested by living bodies.

Although capsules can be produced from pullulan, they have been produced using gelatin as a main material. Recently, however, there is a trend that ingredients originated from animals such as gelatin are not preferable because of fear of the pollution by infectious diseases of domestic animals such as bovine spongiform encephalopathy (BSE) and foot-and-mouth disease (FMD). Therefore, it is expected to provide capsules using pullulan as a main material.

Although HPCS has highly useful features as described above, it has a serious disadvantage of being easily affected by the change of humidity. HPCS easily releases moisture under a low humidity condition to affect elasticity. Although glycerin, sugar alcohol, etc. have been conventionally used as plasticizers to improve the disadvantages of HPCS, HPCS prepared with those have disadvantages of absorbing moisture easily and causing adhesion under a high humidity condition.

DISCLOSURE OF INVENTION

Since HPCS, produced by using conventional production technology, have low stability to the change of humidity, they have the disadvantages of requiring a strict regulation of humidity when handled or when produced secondary processing products using the shaped products as materials, and accompanying various difficulties on the handling of products. The first object of the present invention is to overcome the above disadvantages and establish HPCS in film, sheet, and capsule forms, having a satisfactory stability to the change of humidity. The second object of the present invention is to provide a process for producing HPCS having a satisfactory stability to the change of humidity. The third object of the present invention is to provide the uses of HPCS prepared by the process.

To solve the above objects, the present inventors have extensively studied from the viewpoint of the uses of various sacchareides. As a result, unexpectedly, the present inventors newly found that HPCS, having a satisfactory stability to the change of humidity, can be produced by incorporating α,α-trehalose thereunto. The present inventors accomplished the present invention by establishing a novel HPCS, its preparation and uses.

BEST MODE FOR CARRYING OUT THE INVENTION

A satisfactory stability to the change of humidity of HPCS as referred to as in the present invention means a property of keeping the shape and quality even in the case of releasing moisture from HPCS or absorbing moisture by HPCS a little when preserved HPCS under a relatively low or high humidity condition. Specifically, it means that the shaped products show no change of the exterior shape, forming cracks, and fragility by drying under a relatively low humidity condition, or no change of the exterior shape, stringiness of the surface, and adhesion between films or to preservation vessels by absorbing moisture under a relatively high humidity condition.

Pullulan is a natural polysaccharide which is produced extracellularly by *Aureobasidium pullulans* when cultivated with starch hydrolyzates as a carbon source. Usually, pullulan having a molecular weight in the range of 20,000-4,000,000, desirably, 50,000-2,000,000, is preferably used to produce HPCS of the present invention. Low molecular pullulan having a molecular weight lower than 20,000 is not preferable because its aqueous solution shows a remarkable fluidity and is hard to shape. High molecular pullulan having a molecular weight of larger than 4,000,000 is too viscous to produce aqueous solutions at a high concentration, and causes the deterioration of handleability.

For example, "PULLULAN PF-10", a pullulan having an average molecular weight of 100,000; and "PULLULAN PF-20" and "PULLULAN PI-20", pullulans having an average molecular weight of 200,000 are commercialized by Hayashibara Shoji Inc., Okayama, Japan, and usable in the present invention. If necessary, derivatives of pullulan modified partially and chemically, can be arbitrarily used. Further, pullulan products with a suitable amount of α,α-trehalose can be arbitrarily used.

α,α-Trehalose is a non-reducing saccharide composed of two glucose molecules bound together via the α,α-1,1 glucosidic linkage. The saccharide has 45% sweetening power of sucrose, superior stability, and compatibility with aqueous pullulan solutions. α,α-Trehalose can be used in the present invention independently of its origin. α,α-Trehalose obtainable from various origins, for example, those obtainable by extracting from yeasts as disclosed in Japanese Patent Kokai No. 246,097/95, those obtainable from maltose by using phosphorylases as disclosed in Japanese Patent Kokai No. 216,695/83, and those obtainable from starch by using enzymatic saccharification as disclosed in Japanese Patent Nos. 170,977/95 and 213,283/95, can be arbitrarily used.

In the case of adding α,α-trehalose to aqueous solutions for producing HPCS, both powdery and aqueous products of α,α-trehalose can be used. For example, "TREHA®", a high-purity hydrous crystalline trehalose commercialized by Hayashibara Shoji Inc., Okayama, Japan, can be advantageously used.

If necessary, one or more substances of high molecular substances except for pullulan, functional substances, seasonings, spices, colorings, flavors, emulsifiers, plasticizers can be used with pullulan as materials for HPCS. Physical properties of HPCS such as solubility, transparency, tactile impression, texture, plasticity, etc. can be changed with additives.

Substances having compatibility with aqueous pullulan solutions are desirable as the high molecular substance except for pullulan. For example, starchy substances such as dextrin and amylose, starch derivatives such as hydroxyethyl-starch, natural polysaccharides such as cellulose, alginic acid, dextran, chitin, and agarose, their derivatives, and proteins such as casein and gelatin can be preferably used.

The natural polysaccharides usable in the present invention mean polysaccharides originated from animals, plants, and microorganisms and those naturally occurred or artificially produced by culturing microorganisms. If necessary, substances which are insoluble or hardly soluble in water or those which are not compatible with aqueous pullulan solutions can be used as fillers or excipients together with pullulan to produce HPCS. In such case, HPCS can be advantageously used to increase hydration by using together with additives such as emulsifier and dispersing agent.

Pharmaceuticals having a medicinal benefit such as anti-inflammatory anodynes, anti-inflammatory steroids, anti-histaminic agents, antibiotics, chemotherapy agents, herb medicines, lysozyme chloride, tranexamic acid, sorbic acid, hinokitiol, cetylpyridinium, alkylglycine, tannnin, sodium fluoride, photosensitizer, and the like; preservatives such as sorbic acid, propionic acid, and the like; enrichments such as royal jelly, polyphenols, propolis extracts, vitamins, minerals, and amino acids and the like; and other such as vegetable powders and extracts, various dietary fibers, and functional saccharides can be used as functional substances.

The seasonings usable in the present invention include sweeteners with a high sweetness such as saccharine, L-aspartyl L-phenylalanine methyl ester, stevioside, α-glycosyl stevioside, rebaudioside, α-glycosyl rebaudioside, glycyrrhizin, sucralose, and the like; seasonings such as soy sauce, miso, amino acids, nucleic acids, and the like; and acidifiers such as various organic acid and the like.

The spices usable in the present invention include orange oil, lemon oil, mint oil, cinnamon oil, eucalyptus oil, spearmint oil, peppermint oil, menthol, and furthermore, plants such as mustard, "wasabi" (Japanese horse-radish), "shiso" (Japanese labiate), and the like; and their powders or extracts.

The colorings usable in the present invention include edible pigments, β-carotene, water-soluble annatto. The flavors usable in the present invention include anisaldehyde, cinnamic acid, L-menthol, lactonic acid, and the like. The emulsifiers usable in the present invention include various fatty acid esters.

In the case of using HPCS for foods, materials except for pullulan are desirably selected from foods or food ingredients for not ruining the edibility. Emulsifiers, plasticizers, and the like are desirably used as low as possible as far as gaining effect of additives for not ruining the taste.

HPCS of the present invention comprises pullulan in an amount of 30% (w/w) or higher (throughout the specification, "% (w/w)" is abbreviated as "%" hereinafter, unless specified otherwise), desirably, 40% or higher, on a dry solid basis. In the case of HPCS having a pullulan content of lower than 30%, characteristic properties of shaped products comprising pullulan such as adhesion and fragility can not be expected when exposed to the change of humidity. Therefore, even in the case of incorporating α,α-trehalose with HPCS, remarkable effects on the properties such as a moisture-retaining ability and resistance to humidity can not be obtained.

Shaped products produced by pouring an aqueous solution comprising pullulan or by shaping that with a certain mold, for example, films, sheets, and capsules can be used as HPCS. If necessary, solids with an unfixed form, which are prepared by crashing shaped products, can be used.

As disclosed in Japanese Patent Kokai No. 13,565/79, pullulan films, as HPCS, can be produced by the steps of pouring an aqueous pullulan solution over a heated-rotary drum or an endless conveyer belt and detaching the resulting film from the heated-rotary drum or the endless conveyer belt when the moisture content of the film is reached to 4-13% by evaporating the moisture of the aqueous pullulan solution. Also, as disclosed in Japanese Patent Kokai No. 111,817/84, pullulan films can be continuously produced by the steps of pouring an aqueous pullulan solution over a heat-resistant plastic film, drying the film by passing through a hot air, stopping the heating when the moisture content of the films reached to a constant value of 4-13% by evaporating the moisture of the aqueous pullulan solution, and detaching the films.

Although pullulan concentration of a material aqueous pullulan solution, which is preferable to produce HPCS, is varied depending on the molecular weight of pullulan and other additives, it is usually, in the range of 5-85%, desirably, 10-50%. In the case of using an aqueous pullulan solution with a lower pullulan concentration, the solution may be flowed on a synthetic plastic film used as a plate for shaping, and required more energy and a long time for heating and drying. In contrast, in the case of using an aqueous pullulan solution with a higher pullulan concentration, it is required a long time to dissolve a pullulan powder, and the handleability of the solution is deteriorated because of its high viscosity even when handled at a relatively high temperature.

The temperature used for preparing aqueous pullulan solutions and using the solution for shaping is usually in the range of 15-95° C., desirably, 50-80°. In the case of preparing an aqueous pullulan solution at a relatively low temperature, it will require a longer time to dissolve pullulan. In the case of shaping the pullulan solution at a relatively low temperature, the solution increases in viscosity and this lowers the drying efficiency. On the contrary, in the case of preparing an aqueous pullulan solution at a relatively high temperature of the solution, it becomes dangerous in working. Further, depending on the types of additives, disadvantages such as denaturing, evaporating, and scattering of additives may be occurred when added those to aqueous pullulan solutions.

The α,α-trehalose content to the main material, pullulan, is preferable in the range of 0.1-90%, desirably, 0.5-60%, on a dry solid basis. In the case of preparing HPCS having a relatively low α,α-trehalose content, the stabilizing effect of α,α-trehalose to the change of humidity is not expectable. In the case of preparing HPCS having a relatively high α,α-trehalose content, it will be difficult to be shaped into a shaped product or the resulting shaped product becomes very fragile and difficult to be handle.

If necessary, an appropriate amount of conventional plasticizers such as glycerin, sugar alcohol, and the like can be advantageously used together with pullulan to produce HPCS. The use of such plasticizers together with HPCS facilitates sealing of HPCS by heating and producing products in a bag form.

Detergents having an emulsifying activity, for example, several fatty acid esters are used as detaching agent for producing films. Sucrose-fatty acid ester, as a detaching agent for producing pullulan films, is added usually in the range of 10% or lower, more preferably, 0.05-5% to pullulan as the main material. In the case of using a relatively low content of the ester, detaching ability of pullulan films from a holding-base material such as synthetic plastic films and metal plates is deteriorated. In the case of using a relatively high content of the ester, HPCS becomes cloudy and loses transparency. Further, HPCS will be hard to dry by detaching during the process of drying.

α,α-Trehalose and other additives can be separately dissolved in water when an aqueous solution is prepared to produce HPCS containing α,α-trehalose. A premix of α,α-trehalose and other additives can be also advantageously used.

Pullulan content in a shaped product can be measured by the method comprising:

extracting pullulan from the shaped product with water or hot water;

hydrolyzing the extracted pullulan by pullulanase to form maltotriose; and quantifying the amount of the formed maltotriose.

HPCS can be used as cosmetics and pharmaceuticals such as packs, cachous, poultices, solidification materials for various medicines, medicine-administration materials for transdermal or trans-mucosal absorption, sustained-release materials, and packing materials.

As described above, since HPCS produced by the present invention has a satisfactory stability to the change of humidity, it is not necessary to strictly control humidity for preserving high pullulan content products or its secondary-processed products in comparison with conventional products. Further, since it is not necessary to consider environmental condition, particularly, a plant for controlling humidity strictly, during the secondary-processing of HPCS of the present invention, the operating efficiency is remarkably improved.

The following experiments explain pullulan films as examples of HPCS of the present invention, which are most easily affected by the change of the humidity:

Experiment 1

Test Using Pullulan Films (Methods)

Throughout the experiment, the stability of pullulan films to the change of humidity and their solubility were evaluated as follows:

Tests for moisture-retaining ability and hygroscopicity were carried out in a temperature-controlled room at 25° C. In the tests, the weight of a pullulan film, which had been preserved at RH 52.8% to be equilibrated, was used as a standard weight. Each pullulan film was preserved under a high or low humidity condition. Increased- or decreased-weight of pullulan films from the above standard weight was measured, and the amount of released-moisture (%) or the amount of absorbed-moisture (%) was calculated.

The calculation formula is as follows:

$$\text{The value } (\%) = [(S-X)/S] \times 100$$

S: the standard weight of a pullulan film,

X: the weight of a pullulan film after preservation.

Plus or minus value means a released- or absorbed-moisture content.

Humidity-controlled desiccators equilibrated at RH 33.0% using an aqueous solution saturated with magnesium chloride, RH 52.8% using an aqueous solution saturated with magnesium nitrate, and RH 80.7% using an aqueous solution saturated with potassium bromide were used in the test. Samples for testing were put into open aluminum vessels and preserved in the desiccators.

The moisture-retaining ability of pullulan films was defined as properties of showing a relatively low moisture-releasing ability (low content of released-moisture) when preserved under a relatively low humidity condition, no change of the exterior shape, no crack by drying, and of no fragility. To examine the moisture-retaining ability, a pullulan film, pre-equilibrated in a desiccator with a humidity controlled at RH 52.8%, was preserved in a desiccator with a humidity controlled at RH 33.0% for 48 hours. The amount of moisture released from a pullulan film was weighed at regular intervals, and the change of the exterior shape was also observed. A denotation, "Yes", for moisture-retaining ability means that the film showed a relatively small amount of released-moisture, and a little or no change of the exterior shape and elasticity accompanying with deterioration. The denotation, "No", means that the film showed a relatively large amount of released-moisture, a change of shape, a decrease of elasticity accompanying with deterioration.

The elasticity of pullulan films was estimated by a criterion whether the films were cracked/broken or not by bending and stretching the films at an angle of 180° to the same direction. The denotation, 'Yes', means that the film was not cracked by bending the film five times similarly as above. The denotation, "No", means that the film was crashed by bending the film once. The denotation, "F (fragile)" means the film showed an intermediate property of those.

The resistance to humidity of pullulan films was defined as properties of showing a relatively low moisture-absorbing ability (low content of absorbed-moisture) when preserved under a relatively high humidity condition, small change of the exterior shape, the properties of the surface, and adhesion or melting. To examine the resistance to humidity, a pullulan film, pre-equilibrated in a desiccator with a humidity controlled at RH 52.8%, was preserved in a desiccator with a humidity controlled at RH 80.7% for 48 hours. The amount of moisture absorbed by the pullulan film was measured by weight at regular intervals, and the change of the exterior shape was also observed. The denotation, "Yes", in resistance to humidity means that the film showed a relatively small amount of absorbed-moisture, and a little or no change of the exterior shape and surface, and a little or no adhesion. The denotation, "No", means that the film showed a change of shape and surface, and adhesion.

The adhesion of pullulan films was judged based on the following five levels by observing the properties of the films drawn out aluminum vessels after the steps of piling few test samples, putting the samples into a desiccator with a humidity controlled at RH 80.7%, and preserving in the desiccator for 48 hours:

A: The films were melted to collapse the shape and adhered to the aluminum vessel tightly;
B: The films adhered each other and also to the vessel tightly;
C: The films adhered each other and also to the vessel, but were detached easily;
D: The films adhered each other slightly, but not to the aluminum vessel; and
E: No adhesion was observed.

The solubility of pullulan films was judged by measuring the time required to break their shape by dissolving in water after the steps of cutting a pullulan film, equilibrated in a desiccator with a humidity controlled at RH 52.8%, to prepare a slip with 15 mm in width, and soaking about 20 mm of the ends of the slip into 500 ml of deionized water at 25° C. in a beaker. The denotation, "Yes", means that the film required two-fold or lower time for dissolving in comparison with the case of a control preparation containing only pullulan and fatty acid ester.

Experiment 1-1

Effects of Various Additives on the Properties of Pullulan Films

To examine the effects of various additives on the properties of pullulan films, material aqueous pullulan solutions were prepared according to the compositions shown in Table 1 and then prepared into pullulan films by the following method. Eighty grams of "PULLULAN PI-20", a commercially available pullulan powder and 0.1 gram of a fatty acid ester (sucrose monolaurate) were admixed with 272 grams of deionized water and completely dissolved by heating. Successively, forty-four grams either of the solution was weighed and placed into a vessel, admixed with 1.0 gram of glycerin, sorbitol, sucrose, α,α-trehalose ("TREHA®"), maltitol, or deionized water. After dissolved completely, each solution was removed bubbles under a reduced pressure, and the vessel was preserved in hot water at 60° C. Each material solution was poured over a synthetic plastic film to prepare a pullulan film with a 150 mm in width, 500 mm in length, and 175 μm in thickness using a YBA-type baker applicator commercialized by Yoshimitsu Seiki Co., Ltd., Tokyo, Japan. The film was dried uniformly using an air-dryer and the drying was stopped when the moisture content of the film reached a constant value. After drying, the plastic film was detached from the pullulan film, and the resulting each pullulan film for tests was put into a plastic bag, sealed and preserved. The thickness of each of the resulting pullulan film was 29±2 μm.

Compositions of material aqueous pullulan solutions to prepare pullulan films for tests were shown in Table 1. The results of the tests for moisture retaining ability, resistance to humidity, and solubility were shown in Table 2.

TABLE 1

| Amount | Composition | | | | | |
|---|---|---|---|---|---|---|
| 10.0 g | Pullulan | Pullulan | Pullulan | Pullulan | Pullulan | Pullulan |
| 0.01 g | FAE | FAE | FAE | FAE | FAE | FAE |
| 1.0 g | Glycerin | Sorbitol | Sucrose | Tre | Maltitol | D.W. |
| 34.0 g | D.W. | D.W. | D.W. | D.W. | D.W. | D.W. |

FAE; Fatty acid ester (sucrose monolaurate)
Tre; α,α-Trehalose
D.W.; Deionized water

TABLE 2

| | Moisture-retaining ability | | | Resistance to humidity | | | Solubility | |
|---|---|---|---|---|---|---|---|---|
| Additive | RM (%) | Elasticity | Judgement | AM (%) | Adhesion | Judgement | TD (sec) | Judgement |
| Glycerin | 2.18 | F | No | 13.67 | B | No | 2.02 | Yes |
| Sorbitol | 2.02 | F | No | 11.76 | C | No | 2.95 | Yes |
| Sucrose | 2.04 | F | No | 9.55 | D | No | 2.62 | Yes |
| α,α-Trehalose | 1.78 | Yes | Yes | 9.40 | E | Yes | 2.49 | Yes |
| Maltitol | 1.79 | Yes | Yes | 10.66 | C | No | 2.32 | Yes |
| None (D.W.) | 2.32 | No | No | 7.92 | E | Yes | 1.90 | — |

RM; Amount of released-moisture,
AM; Amount of absorbed-moisture,
TD; Time required for dissolving,
F; Fragile,
D.W.; Deionized water.

As shown in Table 2, a film with no additive showed a maximum released-moisture level and had an unsatisfactory moisture-retaining ability. In contrast, a film prepared with α,α-trehalose or maltitol showed a lower released-moisture level and was estimated to have improved moisture-retaining ability. The films showed a lower released-moisture level, no change in exterior shape, and no deterioration of elasticity even when equilibrated at a RH 52.8% and preserved at a RH 33.0% for 48 hours. The films prepared with glycerin, sorbitol, or sucrose and those prepared with no additive showed a higher released-moisture level and dried. Furthermore, the change of exterior shape and the deterioration of elasticity to crack by bending once to fifth were observed on a part of the films.

The pullulan film prepared with α,α-trehalose and that with no additive were estimated to be a film showing a relatively small deterioration of resistance to humidity. Those films showed relatively low absorbed-moisture level, no change of the exterior shape and surface of films, and no adhesion between two films and to aluminum vessels even when equilibrated at a RH 52.8% and preserving at a RH 33.0% for 48 hours. Although a pullulan film prepared with sucrose showed a relatively low absorbed-moisture level, adhesion between films was frequently observed. The pullulan film prepared with glycerin, sorbitol, or maltitol showed a relatively high absorbed-moisture level and adhesion ability to an aluminum vessel.

From the results described above, it was revealed that only α,α-trehalose was effective as an additive in keeping both moisture-retaining ability and resistance to humidity. Since the solubility of a pullulan film prepared with α,α-trehalose was not decreased in comparison with other films, the film can be used as a material for foods, cosmetics, and pharmaceuticals.

Experiment 1-2

Effect of α,α-Trehalose Content on Physical Properties of Pullulan Film

In order to examine the effect of α,α-trehalose content on the physical properties of pullulan film, several material aqueous solutions were prepared by dissolving "PULLULAN PI-20", a commercially available powdery pullulan, and a fatty acid ester (sucrose monolaurate) in deionized water heated to 80° C. to give material aqueous solutions with compositions in Table 3, and then admixed with "TREHA®", an α,α-trehalose product, to give the concentrations described in Table 3. After removing bubbles under a reduced pressure, each of the material aqueous solution was poured over a synthetic plastic film to give 150 mm in width, 700 mm in length, and 175 μm in thickness using a YBA-type baker applicator commercialized by Yoshimitsu Seiki Co., Ltd., Tokyo, Japan. The resulting films were uniformly dried using an air dryer and the drying was stopped when reached a constant moisture content. After drying, the synthetic plastic films were torn and the resulting pullulan films for various tests were put into plastic bags and preserved under sealed condition. The thickness of the pullulan films was 29±2 μm.

Compositions of the material aqueous solutions for pullulan films were in Table 3. The results of tests for moisture-retaining activity, resistance to humidity, and solubility of the pullulan films were shown in Table 4.

TABLE 4

| Property | Test No. | | | | | | | |
|---|---|---|---|---|---|---|---|---|
| | T1 | T2 | T3 | T4 | T5 | T6 | T7 | T8 |
| Moisture-retaining ability | No | No | Yes | Yes | Yes | Yes | Yes | —** |
| Resistance to humidity | Yes | Yes | Yes | Yes | Yes | Yes | Yes | —** |
| Solubility | Yes | Yes | Yes | Yes | Yes | Yes | Yes | —** |
| Elasticity | Yes | Yes | Yes | Yes | Yes | Yes | No* | —** |

*Fragile,
**Not tested. (Could not be shaped)

As shown in Table 4, the pullulan film having an α,α-trehalose content to pullulan of 90% showed a satisfactory moisture retaining ability, resistance to humidity, and solubility. However, the film was slightly fragile and showed a low elasticity after preserving under a low humidity condition. Further, the film was cracked easily by bending. The pullulan film having an α,α-trehalose content to pullulan of 150% could not be shaped well because of forming cracks by drying. Therefore, it is revealed that α,α-trehalose content to pullulan in HPCS is preferable in the range of 0.1-90%, desirably, of 0.5-60%.

Although the following examples concretely explain the present invention in detail, the present invention is not restricted by them:

EXAMPLE 1

Two hundred and fifty parts by weight of "PULLULAN PI-20", a commercially available pullulan, 0.5 part by weight of sucrose monolaurate, a detergent, and 52.5 parts by weight of "TREHA®", α,α-trehalose, were mixed with 700 parts by weight of deionized water and dissolved into a material aqueous solution for film, and then removed bubbles from the solution under a reduced pressure. A pullulan film having a thickness of 30 μm was prepared by the steps of pouring the solution continuously over a synthetic plastic film to spread and drying by passing through hot air of 70° C. The film has a satisfactory stability to the change of humidity, transparency, gloss, and solubility in water, and can be advantageously used as a material for secondary processing such as

TABLE 3

| Material | Test No. | | | | | | | |
|---|---|---|---|---|---|---|---|---|
| | T1 | T2 | T3 | T4 | T5 | T6 | T7 | T8 |
| | Content (g) | | | | | | | |
| Pullulan | 30.0 | 30.0 | 30.0 | 30.0 | 30.0 | 25.0 | 20.0 | 15.0 |
| Fatty acid ester | 0.05 | 0.05 | 0.05 | 0.05 | 0.05 | 0.042 | 0.033 | 0.025 |
| α,α-Trehalose | 0 | 0.003 | 0.03 | 0.15 | 1.5 | 15.0 | 18.0 | 22.5 |
| Deionized water | 70.0 | 70.0 | 69.9 | 69.8 | 68.5 | 60.0 | 62.0 | 62.5 |
| TCP* (%) | 0 | 0.01 | 0.1 | 0.5 | 5.0 | 60.0 | 90.0 | 150.0 |

*TCP; α,α-trehalose content to pullulan an edible and water-soluble wrapping material for foods and piled-shaped product to pinch various substances between films.

EXAMPLE 2

Two hundred parts by weight of "PULLULAN PI-20", a commercially available pullulan, 40 parts by weight of "TREHA®", α,α-trehalose, two parts by weight of citric acid, 0.05 part by weight of L-menthol, five parts by weight of cyclodextrin, 0.05 part by weight of an edible green pigment, and 0.5 part by weight of sucrose monolaurate, a detergent were mixed with 750 parts by weight of deionized water and dissolved into a material aqueous solution for film, and then removed bubbles from the solution under a reduced pressure. A pullulan film having a thickness of 50 μm was prepared by the steps of pouring the solution continuously over a synthetic plastic film to spread and drying by passing through hot air of 60° C. The film has a satisfactory stability to the change of humidity, transparency, gloss, characteristic scent and color, and solubility in water, and can be advantageously used as a food or a material for secondary processing.

EXAMPLE 3

Total 430 parts by weight of mixture consisting 250 parts by weight of "PULLULAN PF-20", a commercially available pullulan, 50 parts by weight of agar, three parts by weight of glycerin, one part by weight of sucrose mono-laurate, a detergent, 125 parts by weight of "TREHA®", α,α-trehalose, and one part by weight of powderized "wasabi", Japanese horseradish were mixed with 570 parts by weight of deionized water and dissolved into a material aqueous solution for film, and then removed bubbles from the solution under a reduced pressure. A pullulan film having a thickness of 50 μm was prepared by the steps of pouring the solution continuously over a synthetic plastic film to spread and drying by passing through hot air of 60° C. The film has a satisfactory stability to the change of humidity, semi-transparency, gloss, solubility in water, and, scent of "wasabi", and can be advantageously used as a material for secondary processing. Further, pieces of the above product, processed by using crasher at a low speed, can be used for candy, confectionery, etc. as a food material possessing a satisfactory solubility.

EXAMPLE 4

Two hundred parts by weight of "PULLULAN PF-20", a commercially available pullulan, five parts by weight of carrageenan, 50 parts by weight of "TREHA®", α,α-trehalose, one part by weight of "POLYPHENON", polyphenols extracted from tea-leaf, 0.05 part by weight of lemon flavor, 0.05 part by weight of decanal, 0.05 part by weight of edible yellow pigment, and 0.2 part by weight of sucrose monolaurate, a detergent were mixed with 750 parts by weight of deionized water and dissolved into a material aqueous solution for film, and then removed bubbles from the solution under a reduced pressure. A pullulan film having a thickness of 30 μm was prepared by the steps of pouring the solution continuously over a synthetic plastic film to spread and drying by passing through hot air of 50° C. The film has a satisfactory stability to the change of humidity, transparency, gloss, and solubility in water, and can be advantageously used as a food or a material for secondary processing.

EXAMPLE 5

Two hundred parts by weight of "PULLULAN PI-20.", a commercially available pullulan, 100 parts by weight of "A-300", a gelatin commercialized by Nitta Gelatin Inc., Osaka, Japan, 30 parts by weight of "TREHA®", α,α-trehalose, and 0.1 part by weight of sucrose monolaurate, a detergent were mixed with 670 parts by weight of deionized water and dissolved into a material aqueous solution for sheet, and then removed bubbles from the solution under a reduced pressure. A pullulan sheet having a thickness of 100 μm was prepared by the steps of pouring the solution continuously over a synthetic plastic film, treated with corona-discharge, to spread and drying by passing through hot air of 70° C. The sheet has a satisfactory stability to the change of humidity, transparency, gloss, and solubility in water, and can be advantageously used as a material for secondary processing.

EXAMPLE 6

Two hundred parts by weight of "PULLULAN PI-20", a commercially available pullulan, 30 parts by weight of "TREHA®", α,α-trehalose, 30 parts by weight of milk casein, five parts by weight of fine powdery "Okiami", krill (Euphausia), five parts by weight of fine powdery pupa, 10 parts by weight of commercially available liquid fish-gathering composition, one part by weight of squid liver-oil, and one part by weight of sucrose monolaurate, a detergent, were mixed with 710 parts by weight of deionized water and dissolved into a material aqueous solution for sheet, and then removed bubbles from the solution under a reduced pressure. A pullulan sheet having a thickness of 50 μm was prepared by the steps of pouring the solution continuously over a synthetic plastic film to spread and drying by passing through hot air of 50° C. The sheet has a satisfactory stability to the change of humidity and solubility in water, and can be advantageously used as an animal-inviting agent such as fishes and insects, possessing a satisfactory solubility, intact or by processing to pieces using crasher at a low speed.

EXAMPLE 7

One hundred and fifty parts by weight of "PULLULAN PF-20", a commercially available pullulan, 25 parts by weight of commercially available hydroxyethyl starch, 125 parts by weight of "TREHA®", α,α-trehalose, 0.1 part by weight of lysozyme chloride, 0.001 part by weight of hinokitiol, and 0.2 part by weight of sucrose monolaurate, a detergent, were mixed with 700 parts by weight of deionized water and dissolved into a material aqueous solution for film, and then removed bubbles from the solution under a reduced pressure. A pullulan sheet having a thickness of 100 μm was prepared by the steps of pouring the solution continuously over a synthetic plastic film to spread and drying by passing through hot air of 50° C. The sheet has a satisfactory stability to the change of humidity, solubility in water, and lysozyme activity. The sheet can be used as a disinfectant, possessing a satisfactory solubility, intact or by processing to pieces by using crasher at a low speed.

EXAMPLE 8

Two hundred parts by weight of "PULLULAN PI-20", a commercially available pullulan, 30 parts by weight of "TREHA®", α,α-trehalose, 20 parts by weight of carboxymethyl cellulose, five parts by weight of L-ascorbic acid 2-glucoside, 0.1 part by weight of "Kankoh-so No. 401", a photosensitizing dye, two parts by weight of α-glucosyl rutin, four parts by weight of 1,2-pentandiol, 1.5 parts by weight of N-acylated sodium L-glutamate, acylated by palm oil fatty acid, one part by weight of potassium hydroxide, 0.2 part by weight of sodium edetic acid, 0.2 part by weight of sodium citrate, and 0.1 part by weight of citric acid were mixed with 730 parts by weight of deionized water and dissolved into a material aqueous solution for film, and then beaten. A pullulan sheet having a thickness of 100 μm was prepared by the steps of pouring the solution continuously over a synthetic plastic film to spread and drying by passing through hot air of 50° C. The sheet has a satisfactory stability to the change of humidity, non-transparency, and solubility in water. The sheet can be advantageously used as a processing material for producing cosmetic pack.

EXAMPLE 9

One hundred and fifty parts by weight of "PULLULAN PF-20", a commercially available pullulan, one part by weight of "SW-J", a carrageenan, two parts by weight of ammonium chloride, and 42.5 parts by weight of "TREHA®", α,α-trehalose as a moisture-retaining-activity improving agent were mixed with 800 parts by weight of deionized water and dissolved into a material aqueous solution, and then removed bubbles from the solution under a reduced pressure. Pins of a capsule-forming apparatus were dipped in the solution kept at 50° C., lift up, and then dried to produce capsules. The capsule has a satisfactory stability to the change of humidity, transparency, gloss, and solubility in water, and can be advantageously used as a filling container for foods and pharmaceuticals.

EXAMPLE 10

Two hundred parts by weight of "PULLULAN PI-20", a commercially available pullulan, 0.5 part by weight of sucrose monolaurate, a detergent, 10 parts by weight of "TREHA®", α,α-trehalose, and 10 part by weight of glycerin were mixed with 780 parts by weight of deionized water and dissolved into a material aqueous solution for film, and then removed bubbles from the solution under a reduced pressure. A pullulan film having a thickness of 30 μm was prepared by the steps of pouring the solution continuously over a synthetic plastic film to spread and drying by passing through hot air of 70° C. The film has a satisfactory stability to the change of humidity, heat-seal adaptability, transparency, gloss, and solubility in water, and can be advantageously used as a material of an edible and water-soluble wrapping material and a secondary processing material such as piled-shaped product pinched various substances between films.

INDUSTRIAL APPLICABILITY

As is evident from the above, according to the present invention, HPCS having a satisfactory stability to the change of humidity can be produced easily and at a relatively low cost by adding α,α-trehalose in a prescribed ratio with a main material, pullulan, to the material aqueous solution for the HPCS production. Further, the present invention enables the operation of the product easily and increases the uses of HPCS.

Since HPCS of the present invention has a satisfactory stability to the change of humidity, HPCS in itself has a satisfactory preservation stability and handleability for a secondary processing. Further, HCPS can be used to improve a preservation stability of products which are obtainable by using HPCS, and can be advantageously used for various uses such as foods, cosmetics, pharmaceuticals, etc.

As described above, the present invention is a significantly important invention that greatly contributes to this art.

The invention claimed is:

1. A shaped product having a high pullulan content consisting of:
   (a) 50 (w/w) % or greater of pullulan on a dry solid basis;
   (b) 5-60 (w/w) % of α,α-trehalose relative to the content of said pullulan in (a) on a dry solid basis; and
   (c) optional plasticizers;
   whereby the content of α,α-trehalose is such that the shaped product is stable to changes in humidity, and wherein said shaped product is in the form of a film, sheet or a film capsule shape.

2. The shaped product according to claim 1, which is a food, cosmetic, or pharmaceutical.

3. The shaped product according to claim 1 wherein the optional plasticizer is selected from the group consisting of glycerin and sugar alcohols.

4. A shaped product having a high pullulan content consisting of:
   (a) 50 (w/w) % or greater of pullulan on a dry solid basis;
   (b) 5-60 (w/w) % of α,α-trehalose relative to the content of said pullulan in (a) on a dry solid basis;
   (c) optional plasticizers; and
   (d) at least one additional substance selected from the group consisting of high molecular substances that are compatible with an aqueous pullulan solution, seasonings, spices, colorings, flavoring ingredients, and emulsifiers;
   whereby the content of α,α-trehalose is such that the shaped product is stable to changes in humidity, and wherein said shaped product is in the form of a film, sheet or a film capsule shape.

5. The shaped product according to claim 4 wherein the high molecular substances that are compatible with an aqueous pullulan solution are selected from the group consisting of dextrin, amylose, hydroxyethyl starch, alginic acid, dextran, chitin, agarose, casein and gelatin.

* * * * *